United States Patent [19]
Bertini et al.

[11] Patent Number: 6,069,172
[45] Date of Patent: May 30, 2000

[54] (R)-2-(3-BENZOYLPHENYL) PROPIONIC ACID SALTS AND PHARMACEUTICAL PREPARATIONS CONTAINING THEM

[75] Inventors: Riccardo Bertini, Poggio Piceaze; Cinzia Bizzarri; Laura Brandolini, both of L'Aquila; Gabriella Melillo; Gianfranco Caselli, both of Milan; Gaetano Clavenna, L'Aquila, all of Italy

[73] Assignee: Dompe' SpA, L'Aquila, Italy

[21] Appl. No.: 09/237,901

[22] Filed: Jan. 27, 1999

[30] Foreign Application Priority Data

Jan. 28, 1998 [IT] Italy ................ MI98A0146

[51] Int. Cl.[7] .................................................. A61K 31/19
[52] U.S. Cl. .......................... 514/570; 514/569; 514/448; 514/255; 562/562; 562/560; 536/23.5; 435/320.1
[58] Field of Search ...................... 514/570, 569, 514/448; 544/394; 562/560; 536/23.5; 435/320.1

[56] References Cited

U.S. PATENT DOCUMENTS

| | | | |
|---|---|---|---|
| 5,808,069 | 9/1998 | Bosone et al. | 544/394 |
| 5,892,017 | 4/1999 | Lee et al. | 536/23.5 |
| 5,895,789 | 4/1999 | Gentile et al. | 514/570 |

OTHER PUBLICATIONS

Ziboh et al., metabolism and function of skin lipids, progress in Lipid research, V27(2), P81–105, 1988.

*Primary Examiner*—Keith D. MacMillan
*Assistant Examiner*—Vickie Kim
*Attorney, Agent, or Firm*—Armstrong, Westerman, Hattori, McLeland, and Naughton

[57] ABSTRACT

A new use of the enantiomer (R)-ketoprofen and of its salts with suitable organic and inorganic bases in the therapy of neutrophil-dependent diseases and phlogistic processes is described as well as pharmaceutical preparations containing such compounds and useful for oral, parenteral or topical administration.

24 Claims, 2 Drawing Sheets

Human PMN neutrophil degranulation inhibition by lanthanum salts and by L-lysine salts of (R)- and (S)-ketoprofen

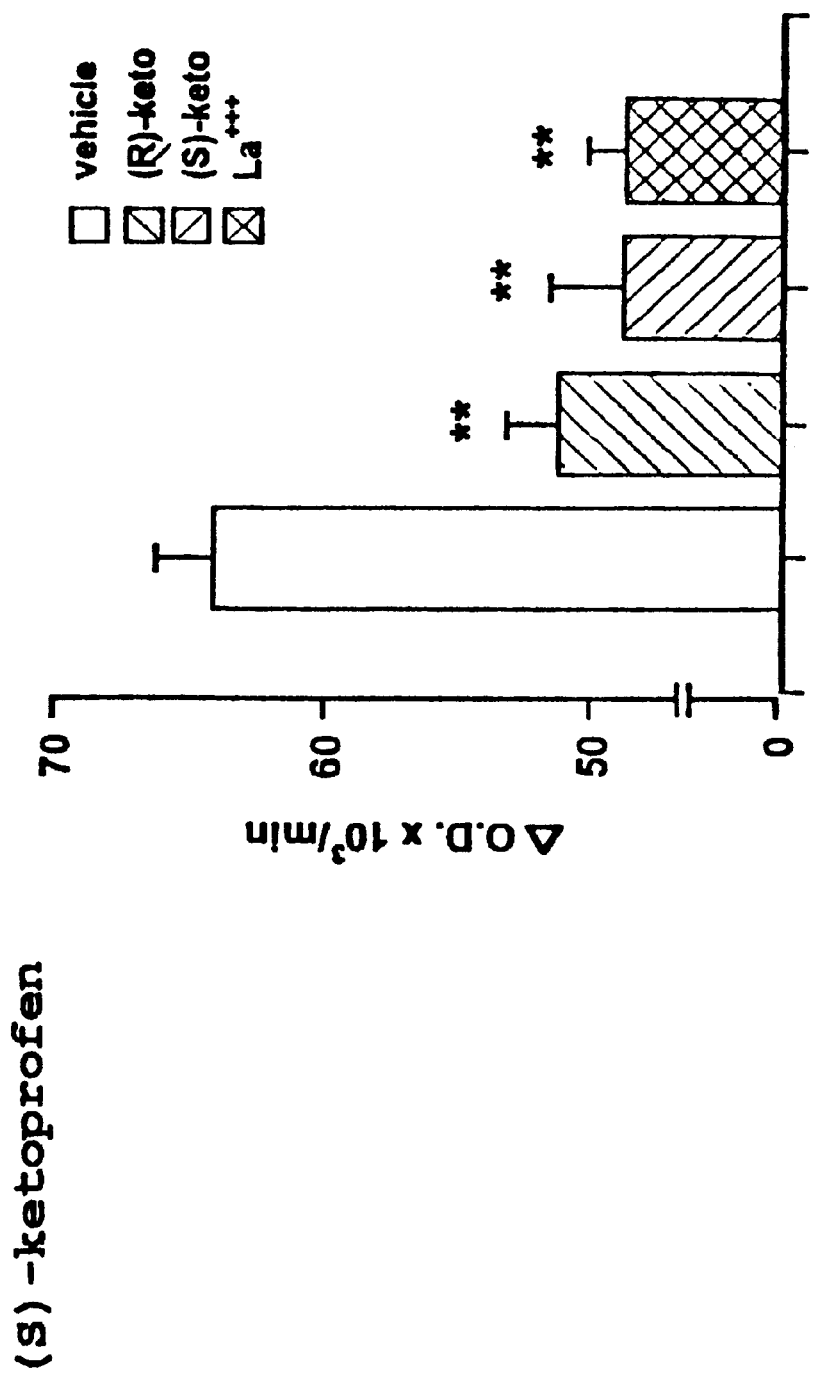
Figure 1. Human PMN neutrophil degranulation inhibition by lanthanum salts and by L-lysine salts of (R)- and (S)-ketoprofen

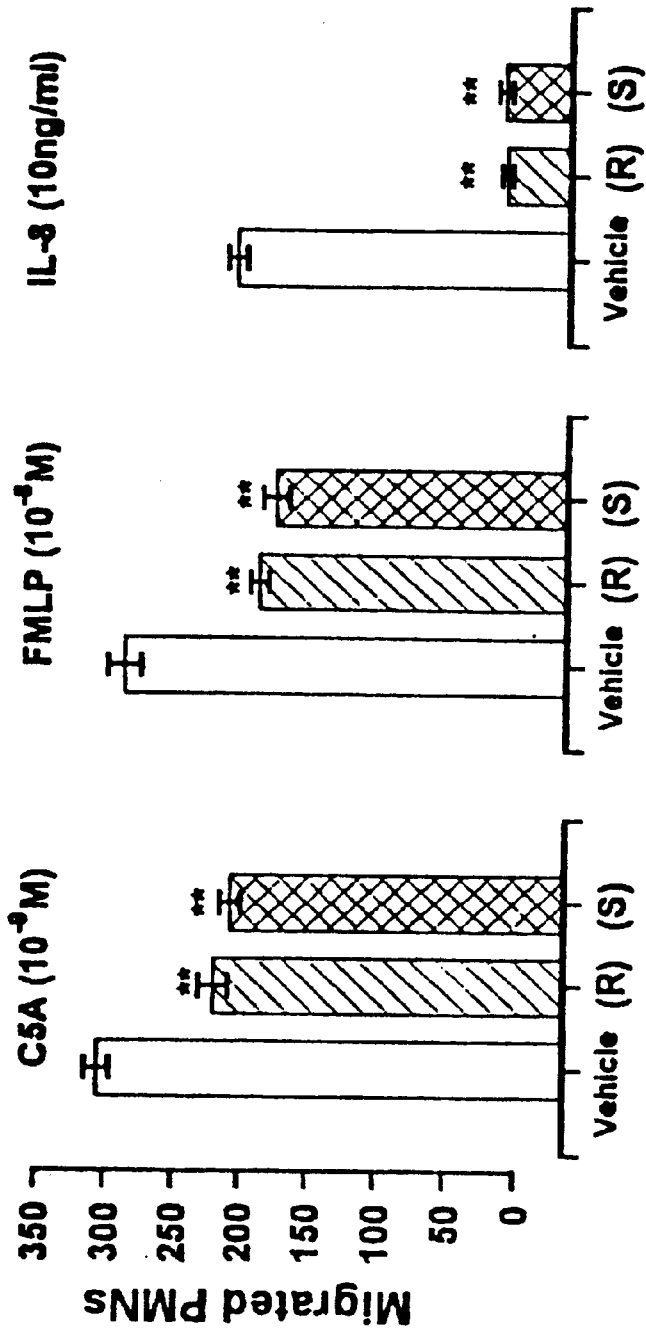
Figure 2. Effects of the L-lysine salts of (R)- and (S)-ketoprofen on chemotactic migration of human PMN neutrophils induced by IL-8, C5a and FMLP

(R)-2-(3-BENZOYLPHENYL) PROPIONIC ACID SALTS AND PHARMACEUTICAL PREPARATIONS CONTAINING THEM

Objects of the present invention are enantiomerically pure salts of (R)-2-(3-benzoylphenyl)propionic acid with achiral and chiral organic bases as well as pharmaceutical preparations containing them, which are used for the therapy of neutrophil-dependent inflammatory diseases such as psoriasis, pulmonary idiopathic fibrosis, acute respiratory failure, damage from reperfusion and glomerulonephritis.

BACKGROUND OF THE INVENTION

From the end of the nineteen eighties it has been known that interleukin-8 (IL-8) is a potent neutrophil agonist. Among other functions IL-8 induces $Ca^{++}$ ion flow into neutrophils, the increase in intracellular $Ca^{++}$ concentration ($[Ca^{++}]_i$) being the starting event which triggers the activation of neutrophils and of other leucocytes, causing L-selectin release, chemotaxis and subsequent degranulation in the presence of cytoclasin C.

Recurring evidence indicates the chemokine IL-8 to be implicated in maintaining, increasing and amplifying neutrophil-dependent inflammatory symptoms which characterize a great number of diseases such as psoriasis (B. J. Nicholoff et al., *Am. J. Pathol.* 138, 129, 1991), rheumatoid arthritis (M. Seitz et al., *J. Clin. Inv.* 87, 463, 1991), ulcerative colitis (V. R. Mahida, *Clin. Sci.* 82, 273, 1992), pulmonary idiopathic fibrosis and acute respiratory failure (P. C. Carré et al., *J. Clin. Invest.* 88, 1802, 1991 and E. J. Miller et al., *Am. Rev. Respir. Dis.* 146, 427, 1992) and also to have a decisive role in amplifying the damage due to reperfusion (N. Sekido et al., *Nature* 365, 654, 1993). In fact, high amounts of IL-8 were found in sputum and in oedematous fluids of patients suffering from chronic inflammatory diseases of the respiratory tract, including from cystic fibrosis up to pulmonary obstructive diseases, such as chronic bronchitis, bronchiectasia, atelectasia, which all are characterized by intrapulmonary accumulation of polymorphonucleate leukocytes (PMN) (J. B. Y. Richman-Eisenstat et al., *Eur. Respir. J.* 6, 1429, 1993 and H. Nakamura et al., *Am. J. Respir. Crit. Care Med.* 149, 1037, 1994).

The more evident characteristics of the above diseases are chronic bacterial infection as well as accumulation of high amounts of PMN neutrophils in the airways. PMN neutrophils in turn are responsible for inducing tissue damage and hypersecretion. The recurring bacterial infections which characterize the often unfavourable disease course, co-operate in increasing these symptoms. *Pseudomonas aeruginosa*, one of the most widespread infecting microorganisms in such diseases, is characterized by the property of inducing and stimulating the production of IL-8 from the epithelial cells of the respiratory tract, so that, contributing to neutrophil activation, it worsens tissue damage, either indirectly, through the release of neutrophil enzymes, such as elastase and catepsins, or directly, causing the formation of $O_2$ radicals and of hypochlorous acid, i.e. of cytotoxic species (P. P. Massion et al., *J. Clin. Inv.* 93, 26, 1994 and P. J. Jorens et al., 263, 1708, 1993).

In experimental models of glomerulonephritis in rabbits, induced by endotoxin or bovine albumin, the intravenous administration of antibodies against IL-8 had a favourable effect as shown by marked decrease of urinary protein excretion, from 3.2 mg/h to 0.9 mg/h, and by prevention of podocyte fusion in the glomerulus (T. Wada et al., *J. Exp. Med.* 180, 135, 1994).

As for other cytokines, the selective inhibition of the synthesis or of the action of IL-8 may result in a therapeutical advantage; one of the possible ways to reach such a goal could be to neutralize cytokine activity in extracellular fluids and in haematic circulation by using antibodies or soluble receptors or proteins able to bind IL-8 as an alternative to the use of receptor antagonists.

4-[3-(4-Fluorophenyl)]-2-[[4-(N-3-(2-quinolinmethoxy)phenyl)]amino]phenylpropylbenzoic acid (ETH-615), a well known leukotriene synthesis inhibitor, clearly inhibited the chemotaxis of PMN leukocytes induced by the cytokine IL-8 or by the leukotriene $LTB_4$, but only slightly inhibited that one induced by N-formyl-methionyl-leucyl-phenylalanine (FLMP or fLMP). Even if it has no effects on T-cell migration stimulated by these agonists, it has been recently proposed in clinical studies for the therapy of inflammatory diseases of the skin, characterized by high levels of leukotrienes IL-8 and $LTB_4$ (M. Kristensen et al., *Exper. Dermatol.* 2, 165, 1993).

The increase of $[Ca^{++}]_i$ in PMN neutrophils is the event which marks and induces their activation following stimulation by different agonists, including, among endogenous stimulants, the leukotriene $LTB_4$, PAF and the C5a factor of the complement, besides IL-8 and the synthetic tripeptide N-formyl-methionyl-leucyl-phenylalanine (FLMP). The transduction of the signal, both at the receptor and post-receptor levels, which causes an increase of $[Ca^{++}]_i$ in these cells, is stimulus-dependent and the production of the superoxide anion may be taken as a measure of said activation.

Leumedine or N-Fmoc-L-leucine (NPC-15669), which belongs to a Fmoc-aminoacid serie, inhibited FLMP-stimulated, but not other agonist-stimulated $[Ca^{++}]_i$ increase in PMN neutrophils (R. J. Smilth et al., *Brit. J. Pharmacol.* 114, 1694, 1995). Other leumedines have been described inhibiting IL-8-mediated accumulation of neutrophils in the respiratory tract of dogs (P. G. Jorensen et al., *Europ. Respir. J.* 7, 1935, 1994).

It is also known that non steroidal antiinflammatory drugs (NSAIDs), while inhibiting the synthesis of prostaglandines (PGs), do not interfere with the production and release of chemotactic chemokines MCP-1 and IL-8. On the contrary, in a comparative study, dexamethasone, in an optimal manner, and some other antirheumatic drugs, such as sodium thiomalate and metotrexate, in a sub-optimal manner, were found to inhibit the release of these cytokines thus suggesting that part of the antirheumatic activity of glucocorticoids may be due to the prevention of the accumulation of chemotactic cytokines acting on neutrophils and monocytes (P. Loetscher et al., *Cytokine* 6, 162, 1994).

So, for example, in human synovial cells the production of IL-8 stimulated by interleukin-1 and TNF-a, was not inhibited by the usual non steroidal antiinflammatory agents, such as thioprofenic acid, indomethacin, naproxen and piroxicam (P. Loetscher et al., Cytokine 6, 162, 1994).

Development of oedema in an inflamed site seems to need the contemporary presence of IL-8 and $PGE_2$, while the single cofactors, administered by intradermal route, were unable to cause oedema formation even if a certain pro-oedemateous effect was described for cytokine IL-8 alone (I. Colditz, ididem 134, 755, 1989).

The use of (±) ibuprofen, or p-isobutylhydratropic acid, and of (±) flurbiprofen, or 3-fluoro-4-phenylhydratropic acid, as well as of their corresponding C1-8-alkyl esters and of pharmaceutically acceptable salts thereof, has been described and claimed for the treatment of respiratory diseases, particularly in the treatment of acute respiratory failure in EP 070 714 (Jul. 5, 1986). (±) Ketoprofen, (±) ibuprofen and (±)flurbiprofen and naproxen are examples of NSAIDs widely used in the therapy of a number of diseases. Ketoprofen, ibuprofen and flurbiprofen are used as racemates, while naproxen is utilized only in the form of the (S) enantiomer. The treated diseases include, besides tooth ache and other painful symptoms, acute inflammation, rheumatic and degenerative diseases of the joints, blood platelet adhesion and, in the case of ibuprofen, also cardiac infarction.

It is believed that, similarly to acetylsalicylic acid, the therapeutic potency and effectiveness of these 2-arylpropionic acids is due to their common property of inhibiting the cyclooxygenase enzyme (CO) which transforms arachidonic acid into algogenic, pro-inflammatory PGs, of which $PGE_2$ is the most representative model.

PGs have an important role in the production of pain, inflammation and fever and, consequently, the above mentioned compounds are used as analgesic, antiinflammatory and antipyretic drugs.

When they are administered as a single dose or as short-term intermittent therapy, they provide suitable analgesia and can clear up pain of slight to moderate intensity, while, in the majority of cases, it is necessary administering them for several days, and also for weeks, in order to obtain a clear antiinflammatory effect.

Even if several comparative studies between single non steroidal antiinflammatory compounds or studies comparing a single compound with many others were published, an overall comparison allowing to build up an effectiveness order list is lacking. It is usually believed that only small differences in activity exist and drug choice by physicians is generally made on an empirical basis. Moreover, the individual responses of patients may greatly vary among each other, so that if a patient does not respond to a given drug, he may be treated with another one. It is however recommended to prefer the use of NSAIDs with the lowest risk of gastroenteric toxicity and at the minimum active dose. More recently it has been supposed that NSAIDs act through the inhibition of two isoforms of the cyclooxygenase (COX-1 and COX-2); the inhibition of COX-1 would be associated with the gastroenteric side effects which are sometimes observed in the treatment with the arylacetic and 2-arylpropionic acids, while those NSAIDs which are highly selective against COX-2 would possess less gastroenteric toxicity (Martindale, *The Extra Pharmacopoeia*, 31st Ed., 72, 1996).

The enzymatic inhibition process of the two isoforms of Co, i.e. COX-1 and COX-2, and consequently the block of the pro-inflammatory, pro-algogenic and pro-pyretic PGs, is a stereospecific process.

Only the (S) enantiomers of the 2-arylpropionic acids, which inhibit $PGE_2$ production, are considered effective as antinflammatory agents (D. Mauleon et al., *Drugs* 52, 24, 1996).

The (R) enantiomers have practically no effect on the enzyme and on PG synthesis; some activity is observed only at very high concentrations, from 100 to 1000 times greater than those of the other enantiomer, and higher than blood levels obtained after administration of these substances ($10^{-9}$–$10^{-6}$M). By consequence the (R) enantiomers of 2-arylpropionic acids were considered for a long period of time as being devoid of any interesting therapeutic utility.

Actually, they are converted in vivo, particularly in the liver and only in negligeable amounts in other tissues such as mouse peritoneal macrofages, into the (S) enantiomers through stereoselective activation of their thio-esters by means of CoA (S. Menzel-Soglowek et al., *Biochem. Pharmacol.* 43, 1487, 1992) and thus they contribute to the global activity of the racemate. The extent to which such bio-conversion takes place in vivo is dependent upon animal species and chemical structure of the compound. So, for instance, the (R) enantiomers of ibuprofen are nearly completely converted into the (S) enantiomers in men and rats, whereas the (R) enantiomers of flurbiprofen and of ketoprofen are practically not converted (<5%) in men and guinea-pigs, but completely converted in rats (K. Brune et al., *Experientia* 47, 257, 1991; K. Brune et al., *J. Clin. Pharmacol.* 32, 944, 1992).

Rats have always been the preferred species for the usual experimental models of inflammation, algesia and hyperalgesia. However, based on the recent studies showing high rate of enantiomeric conversion of 2-arylpropionic acids in this species, it seems not very suitable, since it does not allow to predict the real activity of these compounds in men, where the conversion may not take place or occur only to a very low extent. In fact, only recently the (R) enantiomers of such 2-arylpropionic acids which, like flurbiprofen and ketoprofen, are not metabolically activated in men, were demonstrated to inhibit pain perception in men with an efficacy at least similar to that of the (S) enantiomers (K. Brune et al., *Experientia*, 1991).

In order to predict the therapeutic effect of the racemates in men, it is necessary to know how much the single enantiomers contribute to the global activity, using experimental models excluding metabolic bio-conversion. This is possible utilizing guinea-pigs instead of rats as experimental animal species in the classical experimental model of subplantar carrageenin injection into the right paw (P. Ghezzi et al., *J. Pharmacol. Exp. Ther.*, 1997). This model allows the contemporary evaluation of the inhibition of oedema formation and of hyperalgesia.

The L-lysine salts of (S)- and (R)-ketoprofen were evaluated by means of the aforesaid test in guinea-pigs in comparison with the L-lysine salt of ketoprofen racemate using indomethacin, an achiral arylacetic acid, as positive internal standard. In the dose range from 25 to 750 mmoles/kg, the salt of the (S) enantiomer inhibited oedema formation in a dose-dependent manner, reaching a statistically significant effect at 75 mmoles/kg and the maximal effect at 250 mmoles/kg and showing less effect at higher doses. Also the salt of the (R) enantiomer significantly inhibited oedema formation, but only starting from the 250 mmoles/kg dose; the activity was dose-dependent also in this case, although with a different slope of the dose-effect curve, thus indicating a different mechanism of action. On the contrary, the L-lysine salt of (R)-ketoprofen showed a marked, dose-dependent inhibitory effect on hyperalgesia at doses from 75 to 250 mmoles/kg. This effect was maximal at the highest dose. The L-lysine salt of (S)-ketoprofen displayed only a slight inhibitory effect on hyperalgesia, wich was statistically significant only at the highest dose of 750 mmoles/kg. The anti-oedema and anti-hyperalgesic effects of the L-lysine salt of the racemate were constantly intermediate between those evaluated for the two enantiomers taken alone, thus indicating that, in the absence of any bio-conversion of the (R) enantiomer, the global activity of the racemate is to be attributed to the (S) enantiomer as far as the anti-oedema activity is concerned and to the (R) enantiomer in regard to hyperalgesia inhibition. This conclusion is substantially according to what reported in the aforesaid paper by K. Brune.

Guinea-pigs are a species naturally resistant to the gastrolesive action of NSAIDs, so that it is not possible to compare the two enantiomers in respect to this parameter in this species, unless using very high doses, having no predictive value. To this purpose, rats are necessarily, again, the chosen species, although the least suitable. The results of a comparative study of the L-lysine salts of (S)- ant (R)-ketoprofen using this animal model clearly showed that the (R) enantiomer has less ulcer-inducing properties. The differences among the enantiomers and the racemate were statistically significant starting from the dose of 40 mmoles/kg: at this dose an "ulcer score" of 2 was evaluated for the (R) enantiomer, compared with "ulcer scores" of 3 and 4 for the racemate and the (S) enantiomer, respectively.

A parallel evaluation of the inhibitory effects of (R)- and (S)-ketoprofen L-lysine salts and of racemic ketoprofen L-lysine salt on lipopolysaccharide-stimulated $PGE_2$, TNF-a and IL-1b release from mouse peritoneal macrophages allowed an interesting interpretation of the above disclosed matter. The L-lysine salt of (S)-ketoprofen inhibited $PGE_2$ formation within the whole dose range of $10^{-6}$–$10^{-9}$ M, while the same effect was observed for (R)-ketoprofen only in the range $10^{-6}$–$10^{-5}$ M. On the other hand, surprisingly, the L-lysine salts of (S)-ketoprofen and of the racemate stimulated TNF-a and IL-1b formation in a dose-dependent manner, reaching the statistical significance in the range $10^{-8}$–$10^{-6}$ M in the case of TNF-a, and at the concentration of $10^{-5}$ M in the case of IL-1b. On the contrary the L-lysine salt of (R)-ketoprofen was completely ineffective and did not stimulate the release of these cytokines within the overall $10^{-9}$–$10^{-5}$ M concentration range. Speculatively, the low gastric tolerability of the lysine salts of (S)-ketoprofen and of racemic ketoprofen could be the direct consequence of the stimulation of TNF-a release ("up regulation") (C. B. Appleyard et al., *Am. J. Physiol.*, 270, G-42, 1996) rather than of the blockade of $PGE_2$ synthesis, as it was thought till now. Furthermore, TNF-a "up-regulation" may provide an understanding key of the lower effectiveness of the racemate salt and of the (S)-ketoprofen salt, in comparison with the (R) enantiomer salt, in the control of hyperalgesia, just for the fact that this last enantiomer, differently from the previous ones, does not amplify the formation of the inflammatory cytokines.

These results substantially agree with those obtained in a comparative study on the topic antiinflammatory activity of racemic ketoprofen and of the single enantiomers in the ultra-violet radiation-induced epidermal erythema test in guinea pigs. Protection obtained by the use of the (R) enantiomer was calculated to be 53.1±4.6%, quite similar and of statistically significant (p<0.05) in respect to that obtained with racemic ketoprofen (56.1±3.1), and lower than that obtained with the (S) enantiomer (73.4±4.0%). However, the whole results obtained in other experimental models of inflammation, such as carrageenin-induced oedema in rats and croton oil-induced ear oedema in mice, let the authors to conclude that the in vivo antiinflammatory effectiveness of the (R) enantiomer was significantly lower than those of the racemate and of the (S) enantiomer.

Similar conclusions were drawn by Svesc et al. (*Chirality*, 5, 589, 1993) on the basis of $TBX_2$ synthesis inhibition in human PMN leukocytes and in rat platelets. In this test (R)-ketoprofen was active at doses 2–3 times greater than the (S) enantiomer and the racemate. On the contrary, in an acetic acid-induced inflammation model in rats, interleukin IL-8 production was significantly (p<0.1) reduced from 53.8 pg/ml to 22.4 and 16.9 pg/ml after administration of (±)ketoprofen 200 and 100 mg/kg, respectively (L. M. Wang et al., *Drugs Exper. Clin. Res.*, 23, 1, 1997).

In a study on patients with initial rheumatoid arthritis the administration of 200 mg of ketoprofen for 10 days caused the normalization of the increased chemotactic index and adhesiveness and a reduction of PMN leucocyte fagocytosis, while their bactericidal function was not affected. Moreover, the chemotactic activity induced by zymosan, an activator of the complement, was inhibited both in healthy volunteers as well as in the studied patients (E. Bacino et al., *Clin. Exper. Reumatol.*, 5, 50, 1987).

Successively, the question of a PG-synthesis inhibition-independent antiinflammatory activity of NSAIDs was widely discussed and studied, particularly in relation to the inhibition of human PMN neutrophil activity and to the mechanisms regulating the function of these cells, which are still substantially unknown. So, for example, it was thought that drugs like ketoprofen, flurbiprofen, sudoxicam, fenofren and indomethacin, after the oral administration, inhibited carrageenin-induced formation of pleural exudate in rats due to their ability to inhibit the migration of PMN cells, but not that of monocytes, into the pleural cavity (A. Blackam and R. T. Owen, *J. Pharm. Pharmacol.*, 27, 201, 1975). But, later, it was demonstrated exatly the opposite for some of these drugs, among which ketoprofen (S. C. R. Meacock and E. Ann Kitchen, Future Trends Inflammation, *Proc. Int. Meet.*, 2nd(1975)320, J. P. Giroud et al, Eds, Birkhaeuser, Basel).

More recently it was supposed that in the case of the fenamates, a particular subgroup of NSAIDs, such as flufenamic and tolfenamic acids, the inhibition of neutrophil activation induced by $Ca^{++}$ ionophore and by the chemotactic peptide FLMP (N-formyl-methionyl-leucyl-phenylalanine) was due to the blockade of $Ca^{++}$ ion entry as indicated by the results of trials evaluating $Mn^{++}$ and $^{45}Ca^{++}$ ion flow. Fenamates seem special in this respect, as compared to other NSAIDs, since ketoprofen, which is taken as the typical prostanoid synthesis inhibitor, was completely inactive like nifedipine, an inhibitor of the voltage-independent $Ca^{++}$ channels, and unlike 1-[2-(4-metoxyphenyl-2-[3-(4-metoxyphenyl) propoxy]ethyl]1H-imidazole (SK&F 96365), a non selective $Ca^{++}$ channel blocker (H. Kankaanranta and E. Moilanen, *Molec. Pharmacol.*, 47, 1006, 1995).

BRIEF SUMMARY OF THE INVENTION

It has now been found, and this is the object of the present invention, that the salts of (R)- and (S)-ketoprofen with chiral and achiral organic bases dose-dependently inhibit, at concentrations from $10^{-9}$ to $10^{-6}$ M, corresponding to blood levels observed in men after administration of therapeutic doses, the increase of intracellular $Ca^{++}$ ion concentration induced by IL-8 in human PMN leukocytes.

BRIEF DESCRIPTION OF THE DRAWINGS

In FIG. 1, the results of trials demonstrating the specific inhibitory effects of the lysine salts of (R)- and (S)-ketoprofen and of lanthanum salts on human PMN neutrophil degranulation are reported graphically.

In FIG. 2, the results of trials demonstrating the specific inhibitory effects of the lysine salts of (R)- and (S)-ketoprofen on IL-8-stimulated chemotactic migration are shown.

DETAILED DESCRIPTION OF THE INVENTION

Table 1 shows the results obtained by using, in the experimental model described by C. Bizzarri et al. (*Blood*, 86, 2388, 1995), the diastereoisomeric salts of L-lysine with (R)- and (S)-ketoprofen, prepared as reported by E. Bosone et al. in patent WO 94/20449 (Sep. 15, 1994).

Table 1. Dose-dependent effect of the L-lysine salts of (R)- and (s)-ketoprofen on $[Ca^{++}]_i$ increase induced by IL-8

| Drug concentration | (R)-ketoprofen L-lysine salt $[Ca^{++}]i$ (n) (% ± SEM) | (S)-ketoprofen L-lysine salt $[Ca^{++}]i$ (n) (% ± SEM) |
| --- | --- | --- |
| 0 | 302 ± 11 (62) | 302 ± 11 (62) |
| $10^{-9}$ | 364 ± 29 ( 6) | 289 ± 19 ( 9) |
| $10^{-8}$ | 188 ± 8 (31) | 183 ± 5 (22) |
| $10^{-7}$ | 193 ± 10 (17) | 199 ± 13 ( 4) |
| $10^{-6}$ | 182 ± 15 (11) | 163 ± 18 ( 3) |

The results reported in Table 1 are cumulative data obtained from 8 trials (8 donors who gave their explicit consent, 3 to 7 cells per specimen). Leukocytes were considered responsive to IL-8 stimulation when $[Ca^{++}]_i$ increased by at least 34% of basal value (standardized as 100%). The responses, expressed as percent of basal value of $[Ca^{++}]_i$, are the mean from all responsive cells; standard error of the mean (±SEM) and number of replications (in brackets) are also reported. In each experimental group the percentage of non-responsive cells was less than 30% except in the case of pretreatment with $10^{-6}$ M concentrations of the drugs. IL-8 concentration was 50 ng/ml.

The inhibitory effects displayed by the studied drugs on the response to IL-8 stimulation are to be considered a direct consequence of the selective blockade of $Ca^{++}$ ion inflow into PMN leukocytes, as evidenced by a comparative competion study with lanthanum ions in the presence of IL-8 (see Table 2), rather than the consequence of an interaction with the receptors or of an effect on receptor expression, i.e. on receptor number.

TABLE 2

Rôle of $Ca^{++}$ channels in the inhibitory action of the L-lysine salts of (R)- and (S)-ketoprofen on $[Ca^{++}]i$ increase induced by IL-8

| Treatment | $La^{+++}$ + IL-8 $[Ca^{++}]i$ (n) (% ± SEM) |
| --- | --- |
| None | 179 ± 5 (18) |
| (R)-ketoprofen L-lysine salt | 176 ± 7 (11) |
| (S)-ketoprofen L-lysine salt | 166 ± 7 ( 8) |

Results reported in Table 2 are the cumulative values from 3 trials (3 donors, 3–7 cells per specimen). Human PMN neutrophils were considered responsive to IL-8 stimulation when $[Ca^{++}]_i$ was increased by at least 34% of basal value (standardized to 100%). Responses are expressed as percent of basal $[Ca^{++}]_i$ value and are the mean from the values of all responsive cells. Standard error of the mean (SEM) and number of replications (in brackets) are also reported. The percentage of non-responsive cells was within 30% for all experimental groups. The concentration of ketoprofen L-lysine salt was $10^{-8}$ M, that of $La^{+++}$ 10 μM, and that of IL-8 50 ng/ml.

The obtained results demonstrate a new property of the studied compounds, not known so far, namely to act at the post-receptor level as antagonists of $[Ca^{++}]_i$ increase, which is dependent upon the opening of membrane channels (this process is prevented by lanthanum salts), so that the sequence of events induced by IL-8 in neutrophils through the primary effect of $[Ca^{++}]_i$ increase is prevented. Such sequence of events, also called neutrophilic activation, consists in neutrophil degranulation followed by the release of elastase, catepsin and other enzymes and by chemotaxis.

In FIG. 1 the results of trials demonstrating the specific inhibitory effects of the lysine salts of (R)- and (S)-ketoprofen and of lanthanum salts on human PMN neutrophil degranulation are reported graphically.

Human PMN neutrophils ($10^7$/ml) were stimulated in the presence of cytoclasin B ($10^{-5}$ M) by adding IL-8 (50 ng/ml) and incubating them for 30 min at 37° C. $La^{+++}$ was added 5 min before IL-8 and the lysine salts of (R)- and (S)-ketoprofen 15 min before IL-8. Degranulation was evaluated based on the amount of elastase released in the cell-free surnatant and is expressed as $DOD \times 10^3$/min. Results, reported as the mean ±SD from 3 independent trials (** $p<0.05$ against IL-8), show a parallel effect of the studied substances and are completely according with the proposed mechanism of action.

In FIG. 2 the results of trials demonstrating the specific inhibitory effects of the lysine salts of (R)- and (S)-ketoprofen on IL-8-stimulated chemotactic migration are shown. Moreover, it was found that the effects of these drugs were not limited to IL-8-stimulated chemotaxis, but were also displayed, surprisingly, on the processe induced by other physiological (C5a) and non-physiological (FMLP) stimulants acting, although in different ways, through variations in $[Ca^{++}]_i$.

Neutrophils were incubated at 37° C. in the presence or in the absence (white column) of the lysine salts of (R)- and (S)-ketoprofen ($10^{-6}$ M) for 10 min; their capacity to migrate in response to the stimulants Ca5, FLMP and IL-8 was then evaluated. Results are expressed as the mean ±SD from 3 separated trials (** $p<0.01$ against each group).

In Table 3 results are reported showing the Ca-antagonistic action (intended as inhibition of $[Ca^{++}]_i$ increase) of the L-lysine salts of (R)- and (S)-ketoprofen against the non physiological and physiological stimulants FLMP ($10^{-7}$M) and C5a ($10^{-8}$M). The values are cumulative ones from 6 trials (6 donors, 3–7 cells per specimen). Human PMN neutrophils were considered responsive to stimulation by FLMP and C5a, one of the components of the complement, if $[Ca ++]_i$ increase was greater than 34% of the basal value (which was standardized to 100%). Results are expressed as percent of the basal value of $[Ca^{++}]_i$ and are the mean from the values of all responsive cells. Standard error of the mean (SEM) and number of replications (n, in brackets) are also reported. The percent of non responsive cells was 0 in the case of FLMP stimulation and 50% in the case of C5a stimulation and of treatment with the L-lysine salts of (R)- and (S)-ketoprofen.

TABLE 3

Effect of the L-lysine salts of (R)- adn (S)- ketoprofen on $[Ca^{++}]i$ increase induced by FMLP and C5a

| Treatment | FMLP $[Ca^{++}]i$ (n) (% ± SEM) | C5a $[Ca^{++}]i$ (n) (% ± SEM) |
| --- | --- | --- |
| None | 208 ± 7 (26) | 198 ± 10 (19) |
| (R)-ketoprofen L-lysine salt | 193 ± 6 (19) | 153 ± 4 (19) |
| (S)-ketoprofen L-lysine salt | 214 ± 13 ( 8) | 150 ± 4 (18) |

The above data clearly show that the L-lysine salts of the two enantiomers (R)- and (S)-ketoprofen act as inhibitors of Il-8-induced chemotaxis to inflammation site and degranulation of human neutrophils by preventing the increase in $[Ca^{++}]_i$ induced by this stimulant in these cells. The inhibition of this specific effect of IL-8, as well as of $[Ca^{2+}]_i$ increase induced by the complement (C5a) and by FMLP, is a specific mark, as the increase in $[Ca^{2+}]_i$ is the signal which triggers neutrophil activation to amplify and sustain inflammation, independently from the flogistic stimulus, which may be bacterial or not. The effect of the two enantiomers is the same and is thus not dependent on the steric configuration of the methyl substituent of this 2-arylpropionic acid. Moreover, the inhibitory action is also completely independent of the organic base used for salt formation; if desired, the base may be choosen among D-lysine, arginine, levodropropizine and dextrodropropizine and/or pharmaceutically suitable achiral organic bases, such as the ones commonly used in pharmaceutical technology, namely glucamine, tromethamine, diethylamine, imidazole and glycine.

(R)-Ketoprofen and its salts differ from racemic ketoprofen and from the (S) enantiomer and their salts due to the fact that they do not inhibit the CO enzymes (COX-1 and COX-2) and thus are substantially devoid of the biological effects linked to the inhibition of these isoforms of the enzyme, as are the gastrolesive action and the inhibitory action on platelet aggregation. In this respect, taking $TXB_2$ synthesis inhibition in human blood as an index of the platel antiaggregating properties of the compounds, the concentrations inhibiting by 50% such synthesis ($IC_{50}$) were calculated to be 0.42±0.04, 0.16±0.04 and 9.75±0.75 mM for racemic ketoprofen, (S)-ketoprofen and (R)-ketoprofen, respectively, thus in accordance with their potency in inhibiting the isoform COX-1 of cyclooxygenase.

It thus follows that (R)-ketoprofen and its salts are more suitable than both (S)-ketoprofen and racemic ketoprofen for the preparation of pharmaceutical formulations useful for the treatment of neutrophil-dependent inflammatory diseases such as psoriasis, idiopathic pulmonary fibrosis, acute respiratory failure, damage from reperfusion and glomerulonephritis; their use for the aforesaid uses is completely new and unexpected.

The synthesis of racemic ketoprofen can be performed starting from 4-benzoyl-2-(1-methylprop-2-en-1-yl)phenol according to the process described in Italian patent application nr. MI96A 001683 filed on Aug. 2, 1996 in the name of the Applicant. The optical separation of the two ketoprofen enantiomers and the subsequent preparation of the enantiomerically pure salts of (R)-ketoprofen with chiral and achiral organic bases can be performed according to the process described in patent application WO 94/20499 filed on Sep. 15, 1994 in the name of the Applicant. This patent includes also pharmaceutical preparations containing such salts. Compounds particularly preferred for the uses foreseen in the present invention, are (R)-ketoprofen as free acid and its salts with pharmaceutically acceptable inorganic and organic bases. More particularly are preferred the salts of (R)-ketoprofen with achiral organic bases such as tromethamine and with chiral organic bases choosen among L-lysine, D-lysine, L-arginine, (R)- and (S)-3-(4-phenylpiperazin-1-yl)propan-2,3-diol. The preparation of these single chemical entities and their use for the formulation of pharmaceutical compositions containing them in the form of tablets, capsules, granulated powders, powders, solutions, creams, ointments, suppositories, foams and sprays, liquids, drops and injectable sterile solutions, has already been described.

The scope of the present invention also includes extemporary preparations of the aforesaid salts obtained by means of salifying given amounts of (R)-ketoprofen with equimolecular amounts of a pharmaceutically commonly used aminoalcohol. Aminoalcohols useful for extemporary salification are choosen in the group consisting of ethanolamine, 3-amino-1-propanol, (R)-1-amino-2-propanol, (S)-1-amino-2-propanol, 2-amino-1,3-propandiol, N-(2-hydroxyethyl)pyrrolidine, D-glucamine and L-prolinol, D-glucosamine and N-methylglucosamine. The extemporary salification reaction can be performed in water, in hydroalcoholic solvents, preferably aqueous ethanol, or in low molecular-weight alcohols such as methanol and ethanol.

The amount of active drug, in terms of ketoprofen free acid, to be administered daily depends on the administration route, age and health status of patients. In the case of oral administration the daily dosage varies from 15 to 200 mg and can be administered divided in multiple doses or as a single dose in the case of controlled-release formulations. In the case of administration by injectable route, the daily dosage varies from 5 to 100 mg and may be eventually divided, if desired, in multiple doses. For topical administration, concentrations of from 0.5 to 10% are suitable. In the case of sub-lingual administration, single doses of from 5 to 50 mg can be administered up to a total daily dose not exceeding 200 mg. Single doses of from 5 to 100 mg can be administered by aerosol to reach up to 800 mg as total daily dose by this route. Concentrations of from 0.1 to 2% are foreseen for nasal spray administration, whereas concentrations of from 5 to 10% are used for the preparation of mouth-wash formulations.

In the case of slow-release formulations of (R)-ketoprofen and of its salts, it is possible to combine, in the same formulation, a slow-release form of the active drug with an immediate-release form.

Both types of formulations are well known in the art and are prepared using conventional methods.

In such formulations the supporting mass, constituting from 10 to 80% of the total, may consist of excipients such as lactose, microcrystalline cellulose, powdered cellulose, starch and various maltodextrins, calcium hydrogenphosphate, silica and their mixture in the presence of binding substances (at a concentration of from 2 to 10%), such as polyvinylpyrrolidone, alginates, carboxymethylcellulose sodium, carboxymethylcellulose starch, in the presence or in the absence of lubricants at the concentration of from about 1 to 5%.

EXAMPLE 1

One tablet of (R)-ketoprofen L-lysine salt contains, in milligrams:

| | |
|---|---|
| (R)-ketoprofen L-lysine salt* | 100 |
| insoluble polyvinylpyrrolidone | 10 |
| microcrystalline cellulose | 125 |
| magnesium stearate | 10 |

*the content of active drug may be varied from 23 to 315 mg per tablet.

EXAMPLE 2

An injectable solution of (R)-ketoprofen L-lysine salt distributed, under nitrogen flow, into sealed phials contains, in mg per ml of aqueous solution:

| (R)-ketoprofen L-lysine salt | 80 |
|---|---|
| citric acid | 2.5 |
| sodium hydrate | 1.5 | the pH of the solution being within the range 7.0–7.5.

EXAMPLE 3

To a suspension of 762.8 g (3 moles) of (R)-ketoprofen finely distributed in 3 l of previously de-aerated sterile water add, under shaking and nitrogen bubbling, a solution of 543.57 g (3 moles) of D-glucamine in 1 l of previously de-aerated sterile water und shake to complete solution.

Then dilute the mass by means of a solution containing 37.5 g of citric acid (about 0.195 moles) and 22.5 g of sodium hydrate (0.5625 moles) in 8 l of previously de-aerated sterile water. If necessary add to the obtained solution sodium hydroxide to a pH value between 7.0 and 7.5 Adjust to a final volume of 15 l and shake to be sure that the solution is completely homogeneous. Then filter, under pressure and nitrogen, through 0.22 mm filters, pour in suitable containers screened and protected against light and UV radiation and let into the filling machine for ripartion into glass phials, of desired capacity, which are successively sealed under nitrogen flow.

The composition of the obtained injectable solution is, in mg per ml of solution:

| (R)-ketoprofen D-glucamine salt | 80.42 |
|---|---|
| citric acid | 2.5 |
| sodium hydrate | 1.5 |

EXAMPLE 4

Injectable solutions containing the relevant (R)-ketoprofen salts are obtained by using, for extemporaneous salification, instead of D-glucamine as in Example 3, equimolecular amounts of a pharmaceutically suitable amine choosen among of ethanolamine, 3-amino-1-propanol, (R)-1-amino-2-propanol, (S)-1-amino-2-propanol, 2-amino-1,3-propandiol, N-(2-hydroxyethyl) pyrrolidine, D-glucosamine and L-prolinol and N-methylglucosamine.

EXAMPLE 5

Solve in 100 ml of de-mineralized water 3 g of polyvinylpyrrolidone, 3 g of sodium saccharinate and 11.75 g of D-glucosamine. After solubilization, add 16.67 g of (R)-ketoprofen and shake to complete dissolution.

This solution, if desidered, can be used as binding phase in granulation processes forcasting the use of fluid-bed or "higher shear mixer" type granulators as well as of mixer for wet granulation.

In a fluid-bed granulation process, the aforesaid binding solution will be sprayed on an excipient mixture hav ing the following composition, in grams:

| mannitol | 335 |
|---|---|
| saccharose | 600 |

-continued

| ammonium glycyrrhizzinate | 13 |
|---|---|
| sodium chloride | 7 |
| flavour | 10 |

The resulting granulated powder is dried to a water content of less than 1% and then calibrated by means of a vibrating 1 mm-mesh sieve; if desidered it can be divided into 3 g sachets.

EXAMPLE 6

Granulated powders containing, as active drugs, the relevant (R)-ketoprofen salts, are obtained by using, for extemporaneous salification, instead of D-glucosamine as in Example 5, equimolecular amounts of a pharmaceutically suitable amine choosen among the group of ethanolamine, 3-amino-1-propanol, (R)-1-amino-2-propanol, (S)-1-amino-2-propanol, 2-amino-1,3-propandiol, N-(2-hydroxyethyl) pyrrolidine, D-glucamine and L-prolinol and N-methylglucosamine.

We claim:

1. Method for the treatment of neutrophil-dependent diseases and phlogistic processes in a patient, comprising administering to said patient a composition comprising a pharmaceutically effective amount of the (R)-ketoprofen enantiomer, optionally salified with a suitable base chosen in the group consisting of chiral and achiral organic bases and inorganic bases, and a pharmaceutically acceptable carrier, diluent or excipient.

2. Method for the treatment of neutrophil-dependent diseases and phlogistic processes in a patient, comprising administering to said patient a composition comprising a pharmaceutically effective amount of an (R)-ketoprofen salt with a suitable chiral or achiral organic base, and a pharmaceutically acceptable carrier, diluent or excipient.

3. Method for the treatment of neutrophil-dependent diseases and phlogistic processes in a patient, comprising administering to said patient a composition comprising a pharmaceutically effective amount of the L-lysine salt of (R)-ketoprofen, and a pharmaceutically acceptable carrier, diluent or excipient.

4. Method for the treatment of neutrophil-dependent diseases and phlogistic processes in a patient, comprising administering to said patient a composition comprising a pharmaceutically effective amount of the dextrodropropizine salt of (R)-ketoprofen, and a pharmaceutically acceptable carrier, diluent or excipient.

5. Method for the treatment of neutrophil-dependent diseases and phlogistic processes in a patient, comprising administering to said patient a composition comprising a pharmaceutically effective amount of the levodropropizine salt of (R)-ketoprofen, and a pharmaceutically acceptable carrier, diluent or excipient.

6. Method for the treatment of neutrophil-dependent diseases and phlogistic processes in a patient, comprising administering to said patient a composition comprising a pharmaceutically effective amount of the D-glucamine salt of (R)-ketoprofen, and a pharmaceutically acceptable carrier, diluent or excipient.

7. The method of claim 1, comprising administering the composition orally.

8. The method of claim 1, comprising administering the composition parenterally.

9. The method of claim 1, comprising administering the composition topically.

10. The method of claim 2, comprising administering the composition orally.

11. The method of claim 2, comprising administering the composition parenterally.

12. The method of claim 2, comprising administering the composition topically.

13. The method of claim 3, comprising administering the composition orally.

14. The method of claim 3, comprising administering the composition parenterally.

15. The method of claim 3, comprising administering the composition topically.

16. The method of claim 4, comprising administering the composition orally.

17. The method of claim 4, comprising administering the composition parenterally.

18. The method of claim 4, comprising administering the composition topically.

19. The method of claim 5, comprising administering the composition orally.

20. The method of claim 5, comprising administering the composition parenterally.

21. The method of claim 5, comprising administering the composition topically.

22. The method of claim 6, comprising administering the composition orally.

23. The method of claim 6, comprising administering the composition parenterally.

24. The method of claim 6, comprising administering the composition topically.

* * * * *